United States Patent [19]

King

[11] Patent Number: 5,104,987
[45] Date of Patent: Apr. 14, 1992

[54] ALKOXYLATION OF ACTIVE HYDROGEN-CONTAINING COMPOUNDS

[75] Inventor: Stephen W. King, Scott Depot, W. Va.

[73] Assignee: Union Carbide Chemicals & Plastics Technology Corporation, Danbury, Conn.

[21] Appl. No.: 585,555

[22] Filed: Sep. 20, 1990

[51] Int. Cl.$^5$ .................. C07D 295/00; C07C 41/03
[52] U.S. Cl. .................... 544/401; 544/398; 560/209; 560/227; 560/230; 560/240; 568/606; 568/607; 568/608; 568/609; 568/610; 568/614; 568/618; 568/619; 568/620; 568/621; 568/622; 568/623; 568/624; 568/625; 568/659; 568/660; 568/661; 568/662; 568/663; 568/664

[58] Field of Search ............... 544/398, 401; 568/606–610, 614, 618, 619, 620–625, 659–664, 670, 673, 675, 676, 678, 679, 680; 560/209, 227, 230, 240

[56] References Cited

U.S. PATENT DOCUMENTS

| | | | |
|---|---|---|---|
| 2,934,505 | 4/1960 | Gurgiolo | 260/2 |
| 3,328,306 | 6/1967 | Ellis | 252/90 |
| 3,432,445 | 3/1969 | Oagan et al. | 260/2 |
| 3,607,785 | 9/1971 | Oagan et al. | 252/431 C |
| 3,682,849 | 8/1972 | Smith et al. | 260/615 B |
| 4,098,818 | 7/1978 | Krummel et al. | 260/535 R |
| 4,112,231 | 9/1978 | Weibull et al. | 544/174 |
| 4,210,764 | 7/1980 | Yang et al. | 568/618 |
| 4,223,164 | 9/1980 | Yang et al. | 568/618 |
| 4,239,917 | 12/1980 | Yang | 568/618 |
| 4,254,287 | 3/1981 | Ziegenhain et al. | 568/621 |
| 4,281,087 | 7/1981 | Heuschen et al. | 525/361 |
| 4,282,387 | 8/1981 | Olstowski et al. | 568/618 |
| 4,302,613 | 11/1981 | Yang et al. | 568/618 |
| 4,306,093 | 12/1981 | Yang et al. | 568/618 |
| 4,326,047 | 4/1982 | Yates | 525/507 |
| 4,359,589 | 11/1982 | Brownscombe | 568/618 |
| 4,360,698 | 11/1982 | Sedan | 568/618 |
| 4,375,564 | 3/1983 | Edwards | 568/618 |
| 4,396,779 | 8/1983 | Edwards | 568/618 |
| 4,396,780 | 8/1983 | Shtykh et al. | 568/620 |
| 4,453,022 | 6/1984 | McCain et al. | 568/618 |
| 4,453,023 | 6/1984 | McCain et al. | 568/618 |
| 4,465,877 | 8/1984 | Edwards | 568/618 |
| 4,472,560 | 9/1984 | Kuyper et al. | 526/120 |
| 4,474,678 | 10/1984 | Lutz et al. | 252/174.21 |
| 4,477,589 | 10/1984 | van der Hulst et al. | 502/169 |
| 4,490,561 | 12/1984 | Yang et al. | 568/615 |
| 4,568,774 | 2/1986 | Yang | 568/616 |
| 4,654,417 | 3/1987 | Inoue et al. | 528/416 |
| 4,659,778 | 4/1987 | Williams | 525/107 |
| 4,665,236 | 5/1987 | Edwards | 568/618 |
| 4,721,816 | 1/1988 | Edwards | 568/618 |
| 4,721,817 | 1/1988 | Edwards | 518/618 |
| 4,727,199 | 2/1988 | King | 568/620 |
| 4,754,075 | 6/1988 | Knopf et al. | 568/618 |
| 4,775,653 | 10/1988 | Leach et al. | 502/170 |
| 4,820,673 | 4/1989 | Knopf et al. | 502/167 |
| 4,886,917 | 12/1989 | Knopf et al. | 568/623 |
| 4,892,977 | 1/1990 | Nieh | 568/618 |
| 4,902,658 | 2/1990 | King et al. | 502/159 |
| 4,946,984 | 8/1990 | Hauser | 568/618 |

FOREIGN PATENT DOCUMENTS

| | | |
|---|---|---|
| 0026544 | 4/1981 | European Pat. Off. . |
| 0026546 | 4/1981 | European Pat. Off. . |
| 0026547 | 4/1981 | European Pat. Off. . |
| 0033359 | 6/1981 | European Pat. Off. . |
| 0082569 | 6/1983 | European Pat. Off. . |
| 0085167 | 6/1983 | European Pat. Off. . |
| 0095562 | 12/1983 | European Pat. Off. . |
| 0104309 | 4/1984 | European Pat. Off. . |
| 0180266 | 5/1986 | European Pat. Off. . |
| 0180267 | 5/1986 | European Pat. Off. . |
| 0212820 | 3/1987 | European Pat. Off. . |
| 339426 | 11/1989 | European Pat. Off. . |
| 1462133 | 1/1977 | United Kingdom . |
| 1462134 | 1/1977 | United Kingdom . |
| 1399966 | 7/1985 | United Kingdom . |

OTHER PUBLICATIONS

Dow Chemical U.S.A., Experimental Ethylene Carbonate XAS-1666.OOL Product Bulletin (1982), pp. 4-9.

Texaco Chemical Company, TEXACAR ® Ethylene and Propylene Carbonates Product Bulletin (1987), pp. 23-24.

Enichem Synthesis SpA, Dimethyl Carbonate Product Bulletin, p. 9 (1981).

U.S. patent application Ser. No. 251,432, filed Sep. 30, 1988 (D-16028).

U.S. patent application Ser. No. 251,436, filed Sep. 30, 1988 (D-16043).

U.S. patent application Ser. No. 251,431, filed Sep. 30, 1988 (D-16002).

U.S. patent application Ser. No. 251,434, filed Sep. 30, 1988 (D-15752).

U.S. patent application Ser. No. 251,430, filed Sep. 30, 1988 (D-15857).

U.S. patent application Ser. No. 251,433, filed Sep. 30, 1988 (D-16015).

Kochurovskaya, G. G. et al., Kriobiol. Kriomed., 3, 1977, pp. 76-79.

Turova, N. Y. et al., Chemical Reviews—Uspekhi Khimii, Mar. 1965, pp. 161-185.

Schick, M. J., Nonionic Surfactants, vol. 1, Marcel Dekker, Inc., N.Y. (1967), pp. 28-41.

*Primary Examiner*—Cecilia Shen
*Attorney, Agent, or Firm*—Rose M. Allen

[57] ABSTRACT

This invention relates to a process for the alkoxylation of an active hydrogen-containing compound comprising contacting the active hydrogen-containing compound with an alkylene carbonate in the presence of a mixed metal oxide catalyst under conditions effective to alkoxylate the active hydrogen-containing compound.

81 Claims, No Drawings

ALKOXYLATION OF ACTIVE HYDROGEN-CONTAINING COMPOUNDS

RELATED APPLICATIONS

The following are related, commonly assigned applications, filed on an even date herewith:

U.S. Pat. application Ser. No. 07/585,561; U.S. Pat. application Ser. No. 07/585,560; U.S. Pat. application Ser. No. 07/585,455; U.S. Pat. application Ser. No. 07/585,563; U.S. Pat. application Ser. No. 07/585,564; U.S. Pat. application Ser. No. 07/585,559; U.S. Pat. application Ser. No. 07/585,456; U.S. Pat. application Ser. No. 07/585,459; U.S. Pat. application Ser. No. 07/585,565; and U.S. Pat. application Ser. No. 07/585,556; all of which are incorporated herein by reference.

BRIEF SUMMARY OF THE INVENTION

1. Technical Field

This invention relates to a process for the alkoxylation of active hydrogen-containing compounds comprising contacting an active hydrogen-containing compound with an alkylene carbonate in the presence of a mixed metal oxide catalyst under conditions effective to alkoxylate the active hydrogen-containing compound.

2. Background of the Invention

A variety of products such as surfactants, functional fluids, glycol ethers, polyols, and the like, are commercially prepared by the condensation reaction of alkylene oxides with organic compounds having at least one active hydrogen, generally, in the presence of an alkaline or acidic catalyst. The types and properties of the alkoxylation products depend on, among other things, the active hydrogen compound, the alkylene oxide, and the mole ratio of alkylene oxide to organic compound employed, as well as the catalyst. As a result of the alkoxylation, a mixture of condensation product species are obtained having a range of molecular weights.

In many applications of alkoxylated products, certain of the alkoxylation species provide much greater activity than others. Consequently, alkoxylation processes are desired that are selective to the production of those alkoxylation species. Further, for many of these uses, mixtures of alkoxylation products falling within a narrow range of molecular distribution of reacted alkylene oxide are believed to be superior to alkoxylation products in which a single alkoxylation specie predominates. For example, in a surfactant composition the range of materials on which the surfactant will be required to operate will normally vary. A range of alkoxylation species, even though narrow, will enhance the performance of the surfactant to the variety of materials which it may encounter. Further, mixtures of closely related alkoxylation species can provide a mixture having other improved properties such as in respect to cloud point, freezing point, pour point and viscosity as compared to a single specie. There, however, is a balance, and if the distribution of species becomes too broad, not only are less desirable alkoxylation species diluting the mixture, but also the more hydrophilic or lipophilic components than those in the sought range can be detrimental to the sought properties.

Moreover, a wide range of alkoxylation species can restrict the flexibility in ultimate product formulation using the alkoxylation reaction product. For example, in making oil-in-water emulsion products it is often desired to prepare a concentrated composition that minimizes the weight percent of water. This concentrate may then be diluted with water at the time of use, thereby saving the expense of shipping and storing water. The ability to form a desirable concentrate is generally dependent, in part, on having a narrow distribution of alkoxylation species since if heavier moieties are present, a greater portion of water is usually required otherwise gelling (evidencing product instability) may occur.

The recognition that certain distributions of moles of alkylene oxide to moles of organic compound in alkoxylation products can be important has long been recognized. For example, British Patent Specification No. 1,399,966 discloses the use of ethoxylates having a hydrophilic-lipophilic balance (HLB) of from about 10 to about 13.5 for use in a laundry detergent. In order to provide this HLB, the moles of ethylene oxide reacted per mole of fatty alcohol is described as being critical. In British Patent Specification No. 1,462,133, the sought cleaning composition employed alkylene oxide cosurfactants sufficient to provide even a narrower HLB, i.e., from about 10 to about 12.5. In British Specification No. 1,462,134, a detergent composition is disclosed which uses ethoxylates having an HLB of from about 9.5 to 11.5, with the preferred ethoxylates having an HLB of 10.0 to 11.1.

Thus, with the increased understanding of the properties to be provided by an alkoxylation product, greater demands are placed on tailoring the manufacture of the alkoxylation product to enhance the sought properties. Accordingly, efforts have been expended to provide alkoxylated products in which the distribution of reacted alkylene oxide units per mole of organic compound is limited to a range in which the sought properties are enhanced.

Alkoxylation processes are characterized by the condensation reaction in the presence of a catalyst of at least one alkylene oxide with at least one organic compound containing at least one active hydrogen. Perhaps the most common catalyst is potassium hydroxide. The products made using potassium hydroxide, however, generally exhibit a broad distribution of alkoxylate species. See, for example, M. J. Schick, *Nonionic Surfactants*, Volume 1, Marcel Dekker, Inc., New York, N.Y. (1967) pp. 28 to 41. That is, little selectivity to particular alkoxylate species is exhibited, especially at higher alkoxylation ratios. For example, FIG. 6 of U.S. Pat. No. 4,223,164 depicts the distribution of alkoxylate species prepared by ethoxylating a fatty alcohol mixture with 60 weight percent ethylene oxide using a potassium catalyst.

The distribution that will be obtained in alkoxylation processes can vary even using the same type of catalyst depending upon the type of organic compound being alkoxylated. For example, with nonylphenol, a Poisson-type distribution can be obtained using a potassium hydroxide catalyst. However, with aliphatic alcohols such as decanol, dodecanol, and the like, the distribution is even broader. These distributions are referred to herein as "Conventional Broad Distributions".

Acidic catalysts can also be used, and they tend to produce a narrower, and thus more desirable, molecular weight distributions; however, they also contribute to the formation of undesired by-products and, thus, are not in wide use commercially.

Particular emphasis has been placed on controlling molecular weight distribution of alkoxylation products. One approach has been to strip undesirable alkoxylate species from the product mixture. For instance, U.S. Pat. No. 3,682,849 discloses processes for the vapor phase removal of unreacted alcohol and lower boiling ethoxylate components. The compositions are said to contain less than about 1% of each of non-ethoxylated alcohols and monoethoxylates, less than 2% by weight of diethoxylates and less than 3% by weight of triethoxylates. This process results in a loss of raw materials since the lower ethoxylates are removed from the composition. Also, the stripped product still has a wide distribution of ethoxylate species, i.e., the higher molecular weight products are still present in the composition to a significant extent. To circumvent viscosity problems which would normally exist with straight-chain alcohols, about 20 to 30 percent of the starting alcohol is to be branched according to the patent.

Obtaining a narrower distribution of alkoxylated species at lower epoxide reactant to organic compound mole ratios can be readily accomplished. U.S. Pat. No. 4,098,818 discloses a process in which the mole ratio of catalyst (e.g., alkali metal and alkali metal hydride) to fatty alcohol is about 1:1. Ethoxylate distributions are disclosed for Parts C and D of Example 1 and are summarized as follows:

|  | Part C | Part D |
| --- | --- | --- |
| Primary fatty alcohol | 12 carbons | 12 to 14 carbons |
| Moles of ethylene oxide per mole of alcohol | 3.5 | 3 |
| Product molecular weight | 352 | 311 |
| Average ethoxylation | 3.8 | 2.54 |
| Distribution, % | | |
| $E_0$ | 0.7 | 3.8 |
| $E_1$ | 6.3 | 15.3 |
| $E_2$ | 17.3 | 25.9 |
| $E_3$ | 22.4 | 23.8 |
| $E_4$ | 21.2 | 15.9 |
| $E_5$ | 15.6 | 10.7 |
| $E_6$ | 8.6 | 3.5 |
| $E_7$ | 5.6 | 1.2 |
| $E_8$ | 2.3 | — |

The high catalyst content in combination with the low alkylene oxide to alcohol ratio appears to enable a narrow, low ethoxylate fraction to be produced. However, as the ratio of alkylene oxide to alcohol increases, the characteristic, Conventional Broad Distribution of alkali metal catalysts can be expected. Moreover, even though the disclosed process is reported to provide a narrower distribution of ethoxylate species, the distribution is skewed so that significant amounts of the higher ethoxylates are present. For example, in Part C, over 15 percent of the ethoxylate compositions had at least three more oxyethylene groups than the average based on the reactants, and that amount in Part D is over 16 percent.

European Patent Application No. A0095562, published December 12, 1983, exemplifies the ability to obtain high selectivity to low ethoxylate species when low ratios of ethylene oxide reactant to alcohol are employed as well as the tendency to rapidly lose that selectivity when higher ethoxylated products are sought. For instance, Example 1, (described as a 1 mole EO adduct), which reports the use of a diethylaluminum fluoride catalyst, employs 300 grams of a 12 to 14 carbon alcohol and 64 grams of ethylene oxide and Example 5, (described as a 1.5 mole EO adduct) using the same catalyst, employs a weight ratio of alcohol to ethylene oxide at 300:118. Based on the graphically presented data, the distributions appear to be as follows:

|  | Example 1 | Example 5 |
| --- | --- | --- |
| $E_0$ | 27 | 10 |
| $E_1$ | 50 | 36 |
| $E_2$ | 17 | 33 |
| $E_3$ | 4 | 16 |
| $E_4$ | — | 6 |
| $E_5$ | — | 2 |
| $E_6$ | — | 1 |

Even with a small increase in ethoxylation from the described 1 mole EO adduct to the described 1.5 mole adduct, the distribution of ethoxylate species broadened considerably with more of the higher ethoxylates being produced as can be expected from a Conventional Broad Distribution. It may be that the catalyst is consumed in the reaction process so that it is not available to provide the narrower distributions of alkoxylation product mixtures at the high adduct levels.

Several catalysts have been identified that are reported to provide molecular weight distributions for higher ethoxylates that are narrower than those expected from a Conventional Broad Distribution. In particular, this work has emphasized ethoxylation catalysis by derivatives of the Group IIA alkaline earth metals. Interest in these catalysts, which to date has been confined almost exclusively to the production of non-ionic surfactants, stems from their demonstrated capability for providing hydrophobe ethoxylates having narrower molecular weight distributions, lower unreacted alcohol contents, and lower pour points than counterparts manufactured with conventional alkali metal-derived catalysts.

Yang and co-workers have been granted a series of U.S. patents which describe primarily the use of unmodified or phenolic-modified oxides and hydroxides of barium and strontium as ethoxylation catalysts for producing non-ionic surfactants exhibiting lower pour points, narrower molecular weight distributions, lower unreacted alcohol contents and better detergency than counterpart products prepared by state-of-the-art catalysis with alkali metal hydroxides. See U.S. Pat. Nos. 4,210,764; 4,223,164; 4,239,917; 4,254,287; 4,302,613 and 4,306,093. Significantly, these patents contain statements to the effect that the oxides and/or hydroxides of magnesium and calcium do not exhibit catalytic activity for ethoxylation, although they may function in the role of promoters for the barium and strontium compounds (U.S. Pat. No. 4,302,613).

The molecular weight distributions of the ethoxylates disclosed in these patents, while being narrower than conventional distributions, appear not to meet fully the desired narrowness. For example, FIG. 6 of U.S. Pat. No. 4,223,146 depicts the product distribution of an ethoxylate of a 12 to 14 carbon alcohol and 60 percent ethylene oxide using various catalysts. A barium hydroxide catalyst is described as providing a product mixture containing, as the most prevalent component, about 16 percent of the six mole ethoxylate. The distribution is, however, still relatively wide in that the ethoxylate species having three or more oxyethylene groups than the most prevalent component is above about 19 weight percent of the mixture and the distribution is skewed toward higher ethoxylates. The strontium hydroxide catalyst run which is also depicted on that figure appears to have a more symmetrical distribution but the most prevalent component, the seven mole ethoxylate, is present in an amount of about 14.5 weight percent and about 21 weight percent of the composition had three or more oxyethylene groups than the most prevalent component.

Also, U.S. Pat. No. 4,239,917 discloses ethoxylate distributions using barium hydroxide catalyst and a fatty alcohol. FIG. 7 of that patent illustrates the distribution at the 40 percent ethoxylation level with the four mole ethoxylate being the most prevalent component. Over about 19 weight percent of the mixture has three or more oxyethylene groups than the most prevalent component. FIG. 4 depicts the distribution of ethoxylation at the 65 percent ethoxylation level. The nine and ten mole ethoxylates are the most prevalent and each represent about 13 weight percent of the composition. The distribution is relatively symmetrical but about 17 weight percent of the composition has at least three more oxyethylene groups than the average peak (9.5 oxyethylene groups). Interestingly, comparative examples using sodium hydroxide catalyst are depicted on each of these figures and evidence the peaking that can be achieved with conventional base catalysts at low ethoxylation levels, but not at higher ethoxylation levels.

McCain and co-workers have published a series of European patent applications describing the catalytic use of basic salts of alkaline earth metals especially calcium, which are soluble in the reaction medium. These applications further disclose catalyst preparation procedures involving alcohol exchange in respect to the alkoxy moiety of the metal alkoxide catalytic species. See European Patent Nos. 0026544, 0026547 and 0026546, all herein incorporated by reference. These workers have also disclosed the use of strong acids to partially neutralize and thereby promote the catalytic action of certain alkaline earth metal derivatives. See U.S Pat. No. 4,453,022 and U.S. Pat. No. 4,453,023 (barium-containing catalyst), both herein incorporated by reference.

The calcium-containing catalysts disclosed by McCain et al. provide enhanced selectivities to higher alkoxylate species as compared to mixtures produced using conventional potassium hydroxide catalyst. Indeed, bases exist to believe that these calcium-containing catalysts provide narrower distributions of alkoxylates than those provided by strontium- or barium-containing catalysts. However, there is still need for improvement in providing a narrower yet distribution of alkoxylation products, particularly a distribution in which at least one component constitutes at least 20 weight percent of the composition and alkoxylation products having more than three alkoxyl groups than the average peak alkoxylation component comprise very little of the product mixture.

U.S. Pat. Nos. 4,754,075, 4,886,917 and 4,820,673, herein incorporated by reference, relates to processes for preparing alkoxylation mixtures having relatively narrow alkoxylation product distributions using modified, calcium-containing catalysts. Processes are also disclosed for making alkoxylation catalysts using calcium oxide and/or calcium hydroxide as sources for the catalytically-active calcium. The alkoxylation product mixtures disclosed therein have a narrow and balanced distribution of alkoxylation species. The disclosed product mixtures are relatively free from large amounts of substantially higher alkoxylation moieties, i.e., those having at least three more alkoxyl groups than the average peak alkoxylate specie. It is stated therein that narrow distributions can be obtained where the most prevalent alkoxylation moiety has four or greater alkoxy units, that is, in the regions in which conventional catalysts provide a relatively wide range of alkoxylation species.

U.S. Pat. No. 4,902,658, herein incorporated by reference, relates to heterogeneous (organic polymer-supported) calcium-containing catalysts and the use thereof in the preparation of alkoxylation products, i.e., condensation reaction products of alkylene oxides and organic compounds having at least one active hydrogen. Processes are provided for preparing heterogeneous (organic polymer-supported) calcium-containing catalysts for alkoxylation using calcium oxide or calcium hydroxide as sources for the catalytically-active calcium. Alkoxylation products are provided that have beneficial, narrow molecular weight ranges and are essentially neutral in pH and free from catalyst residues.

Copending U.S. Patent application Ser. No. 251,434, files Sept. 30, 1988, relates to modified calcium-containing catalysts and the use thereof in the preparation of alkoxylation products, i.e., condensation reaction products of alkylene oxides and organic compounds having at least one active hydrogen. Processes are provided for preparing modified calcium-containing catalysts for alkoxylation using calcium metal or a calcium-containing compound, e.g., calcium oxide or calcium hydroxide, as sources for the catalytically-active calcium and at least one divalent or polyvalent metal salt of an oxyacid as a modifier. Processes are also provided for preparing alkoxylation products that have beneficial, narrow molecular weight ranges using the modified calcium-containing catalysts.

Copending U.S. Pat. application Ser. No. 251,430, filed Sept. 30, 1988, discloses the use of calcium sulfate as a catalyst in the preparation of alkoxylation products, i.e., condensation reaction products of alkylene oxides and organic compounds having at least one active hydrogen, that have beneficial, narrow molecular weight ranges.

Copending U.S. Pat. application Ser. No. 251,433, filed Sept. 30, 1988, describes modified calcium-containing bimetallic or polymetallic catalysts and the use thereof in the preparation of alkoxylation products, i.e., condensation reaction products of alkylene oxides and organic compounds having at least one active hydrogen. Processes are provided for preparing modified calcium-containing bimetallic or polymetallic catalysts for alkoxylation using calcium metal or a calcium-containing compound, e.g., calcium oxide or calcium hydroxide, as sources for the catalytically-active calcium. Processes are also provided for preparing alkoxylation products that have beneficial, narrow molecular weight ranges using the modified calcium-containing bimetallic or polymetallic catalysts.

Copending U.S. Pat. application Ser. No. 251,432, filed Sept. 30, 1988, relates to modified Group IIA metal-containing (other than calcium-containing) bimetallic or polymetallic catalysts and the use thereof in the preparation of alkoxylation products, i.e., condensation reaction products of alkylene oxides and organic compounds having at least one active hydrogen. Processes are provided for preparing the modified Group IIA metal-containing bimetallic or polymetallic catalysts for alkoxylation using a Group IIA metal or a Group IIA metal-containing compound, e.g., magnesium acetate, as sources for the catalytically-active Group IIA metal. Processes are also provided for preparing alkoxylation products that have beneficial, narrow molecular weight ranges using the modified Group IIA metal-containing bimetallic or polymetallic catalysts.

Copending U.S. Pat. application Ser. No. 251,436, filed Sept. 30, 1988, discloses modified Group IIIB metal-containing bimetallic or polymetallic catalysts and the use thereof in the preparation of alkoxylation products, i.e., condensation reaction products of alkylene oxides and organic compounds having at least one active hydrogen. Processes are provided for preparing the modified Group IIIB metal-containing bimetallic or polymetallic catalysts for alkoxylation using a Group IIIB metal or a Group IIIB metal-containing compound, e.g., lanthanum oxide, as sources for the catalytically-active Group IIIB metal. Processes are also provided for preparing alkoxylation products that have beneficial, narrow molecular weight ranges using the modified Group IIIB metal-containing bimetallic or polymetallic catalysts.

Copending U.S. Pending application Ser. No. 251,431, filed Sept. 30, 1988, describes modified bimetallic or polymetallic (other than Groups IA, IIA and IIIB metals) catalysts and the use thereof in the preparation of alkoxylation products, i.e., condensation reaction products of alkylene oxides and organic compounds having at least one active hydrogen. Processes are provided for preparing the modified bimetallic or polymetallic catalysts for alkoxylation using a divalent or polyvalent metal or a divalent or polyvalent metal-containing compound, e.g., aluminum isopropoxide, as sources for the catalytically-active metal. Processes are also provided for preparing alkoxylation products that have beneficial, narrow molecular weight ranges using the modified bimetallic or polymetallic catalysts.

European Patent Application No. 339426 relates to an alkoxylation process in which an active hydrogen-containing compound is reacted with ethylene oxide or propylene oxide in the presence of calcined hydrotalcite to provide alkoxylated products having a narrow distribution of homologues.

U.S. Pat. No. 4,775,653 describes a process for preparing an alkoxylation catalyst in which the catalyst pre-mix is formed by admixing an alkoxylated alcohol with a calcium containing compound which is dispersible in the alkoxylated alcohol, an inorganic acid and an aluminum trialkoxide, the pre-mix being heated to a temperature and for a time sufficient to effect at least partial exchange reaction between the alkoxide groups of the aluminum alkoxide and the hydroxyl groups of the alkoxylated alcohol. There is also disclosed an alkoxylation process utilizing the catalysts formed as described above.

U.S. Pat. No. 4,892,977 discloses a process for preparing nonionic surfactants containing a narrow molecular weight distribution which comprises reacting a reactive hydrogen compound selected from the group consisting of monohydric alcohols having from about 6 to 30 carbon atoms with an alkylene oxide having from 2–4 carbon atoms at a temperature at which the reaction proceeds in the presence of at least a catalytic amount of a particular magnesium catalyst containing phosphorus.

Dow Chemical U.S.A., Experimental Ethylene Carbonate XAS-1666.00L Product Bulletin (1982), pp. 4–9, discloses hydroxyethylation reactions in which ethylene carbonate reacts with compounds containing active hydrogen to give hydroxyethyl derivatives. Compounds containing active hydrogen include phenols, thiophenols, alcohols, mercaptans, carboxylic acids, amines and amides. The reactions are carried out at temperatures of from 100° C. to 200° C. in the presence of metal salts such as potassium carbonate. Carbon dioxide is the principle by-product. It is stated that ethylene carbonate yields, in most cases, the mono-ethylene oxide insertion product. At pages 8–9, the use of ethylene carbonate as a monomer for the synthesis of a variety of polymers is disclosed. It is stated that polycarbonates can be produced from the polymerization of ethylene carbonate in the presence of a base and small amounts of diols. It is also stated that polyoxyethylenes or polyglycols can be produced by the homopolymerization of ethylene carbonate at an elevated temperature in the presence of carbonates and bicarbonates of alkali metals and inert materials with a large surface area, e.g., ground glass. Alcohols can also react with excess ethylene carbonate to form polyglycol derivatives.

Texaco Chemical Company, TEXACAR ® Ethylene and Propylene Carbonates Product Bulletin (1987), pp. 23–24, describes hydroxyalkylation reactions in which ethylene carbonate and propylene carbonate react with compounds which contain an active hydrogen, i.e., alcohols, mercaptans, phenols, thiophenols, amines and carboxylic acids, to give the corresponding hydroxyethyl and hydroxypropyl derivatives. The reactions are run at temperatures of 100° C. to 200° C. employing a basic catalyst such or potassium carbonate at a 0.5 weight percent level. At page 24, it is stated that linear polycarbonates may be formed by reacting ethylene carbonate with aliphatic, cycloaliphatic or araliphatic dioxy compounds such as 1,4-dimethylcyclohexane or with diethylene glycol.

Enichem Synthesis SpA, Dimethyl Carbonate Product Bulletin, p.9, discloses the reaction of dimethyl carbonate with glycols or diphenols to yield oligomers or polycarbonates.

DISCLOSURE OF THE INVENTION

This invention relates to a process for the alkoxylation of an active hydrogen-containing compound comprising contacting the active hydrogen-containing compound with an alkylene carbonate in the presence of a mixed metal oxide catalyst under conditions effective to alkoxylate the active hydrogen-containing compound.

This invention also relates to a process for the alkoxylation of active hydrogen-containing compounds which comprises (i) contacting an active hydrogen-containing compound with an alkylene carbonate under conditions effective to produce a carboxylated alkoxylated active hydrogen-containing compound, and (ii) contacting the carboxylated alkoxylated active hydrogen-containing compound with a mixed metal oxide catalyst under conditions effective to decarboxylate the carboxylated alkoxylated active hydrogen-containing compound.

The alkoxylated active hydrogen-containing compounds prepared in accordance with the processes of this invention can exhibit a narrow distribution of alkoxylate species as more fully described hereinafter.

In a preferred embodiment, the processes of this invention can provide alkoxylated active hydrogen-containing compounds such as CARBOWAX ® poly(oxyethylene)glycols resulting from the reaction of ethylene glycol or diethylene glycol and ethylene carbonate with no by-product salt formation. A disadvantage associated with conventional homogeneous based catalyzed alkoxylations is residual salt after neutralization.

In still another preferred embodiment, the processes of this invention can Provide alkoxylated active hydrogen-containing compounds having a selected amount of alkoxylation. In particular, the processes of this invention can enhance selectivity to low mole alkoxylate materials such as CARBITOL ® materials, e.g., 2-(2-methoxyethoxy)ethanol, CELLOSOLVE ® materials, e.g., 2-methoxyethanol, and the like than the conventional processes.

Many active hydrogen-containing compounds such as starches, pentaerythritol, imidazoles, natural amino acids, commercial pectin and disaccharides which are difficult to alkoxylate with ethylene oxide and/or propylene oxide can be alkoxylated under the process conditions described herein.

The alkoxylated active hydrogen-containing compounds produced in accordance with the processes of this invention are useful for a wide variety of applications such as TERGITOL ® nonionic surfactants, CARBITOL ® materials, CELLOSOLVE ® materials, CARBOWAX ® poly(oxyethylene)glycols, UCON ® fluids and lubricants, POLYOX ® poly(oxyethylene)glycols, poly(oxyethylene)(oxypropylene)glycols and the like.

For purposes of this invention, the chemical elements are identified in accordance with the Periodic Table of the Elements, CAS version, Handbook of Chemistry and Physics, 67th Ed., 1986-87, inside cover. Also, for purposes of this invention, Group IIIB metal oxides embraces the lanthanides and actinides. As used herein, the term "oxide" embraces oxides, hydroxides and/or mixtures thereof. Sulfur analogs of active hydrogen-containing compounds, i.e., thiols, are also embraced by this invention.

DETAILED DESCRIPTION

As indicated above, this invention relates to a process for the alkoxylation of active hydrogen-containing compounds comprising contacting an active hydrogen-containing compound with an alkylene carbonate in the presence of a mixed metal oxide catalyst under conditions effective to alkoxylate the active hydrogen-containing compound.

As also indicated above, this invention relates to a process for the alkoxylation of active hydrogen-containing compounds which comprises (i) contacting an active hydrogen-containing compound with an alkylene carbonate under conditions effective to produce a carboxylated alkoxylated active hydrogen-containing compound, and (ii) contacting the carboxylated alkoxylated active hydrogen-containing compound with a mixed metal oxide catalyst under conditions effective to decarboxylate the carboxylated alkoxylated active hydrogen-containing compound.

When an active hydrogen-containing compound and alkylene carbonate are employed as starting materials, it is believed that a ring opening transesterification reaction followed by a decarboxylation reaction occurs to provide the desired alkoxylate product. The exact reaction mechanism is not fully appreciated but what is appreciated is that an active hydrogen-containing compound starting material and alkylene carbonate starting material can be contacted in the presence of a mixed metal oxide catalyst under conditions described herein to provide an alkoxylation product mixture. It is also appreciated that a carboxylated alkoxylated active hydrogen-containing compound can be contacted with a mixed metal oxide catalyst under conditions described herein to provide an alkoxylation product mixture.

Step (i) of certain processes of this invention can in general be referred to as a transesterification reaction or a (poly)carbonate formation reaction. Any suitable transesterification catalyst can be employed in step (i). Such transesterification catalysts are known and include, for example, basic metal oxides, alkoxides and other basic metal salts such as potassium carbonate, sodium titanate and the like. Other suitable transesterification catalysts include, for example, Bronsted acids such as sulfuric acid and Lewis acids such as aluminum triisopropoxide. As discussed hereinafter in regard to the decarboxylation catalyst, the transesterification catalyst employed in this invention likewise may also contain support(s), binding agent(s) or other additives to stabilize or otherwise help in the manufacture of the catalyst. Both homogeneous and heterogeneous catalysts can be employed in the step (i) reaction. The amount of transesterification catalyst used in step (i) is dependent on the particular catalyst employed and can range from about 0.01 weight percent or less to about 10 weight percent or greater of the total weight of the starting materials.

Suitable active hydrogen-containing compound starting materials which can be employed in the step (i) transesterification reaction include any permissible substituted or unsubstituted active hydrogen-containing organic compound(s). Illustrative active hydrogen-containing compound starting materials useful in this invention include, for example, substituted and unsubstituted alcohols, phenols, carboxylic acids, amines and the like. Preferred active hydrogen-containing compounds include alcohols and phenols.

Suitable active hydrogen-containing compounds include substituted and unsubstituted alcohols (mono-, di- and polyhydric alcohols), phenols, carboxylic acids (mono-, di- and polyacids), and amines (primary and secondary). Other suitable active hydrogen-containing compounds include substituted and unsubstituted thiophenols, mercaptans, amides and the like. Frequently, the organic compounds contain 1 carbon to about 100 or 150 carbons (in the case of polyol polymers) and can contain aliphatic and/or aromatic structures. Most often, the organic compounds are selected from the group of mono-, di- and trihydric alcohols having 1 to about 30 carbon atoms. The organic compounds having active hydrogens can be the product of hydroformylation/hydrogenation reactions.

Suitable alcohols include primary and secondary monohydric alcohols which are straight or branched chain such as methanol, ethanol, propanol, pentanol, hexanol, heptanol, octanol, nonanol, decanol, undecanol, dodecanol, tridecanol, tetradecanol, pentadecanol, hexadecanol, octadecanol, isopropyl alcohol, 2-ethylhexanol, sec-butanol, isobutanol, 2-pentanol, 3-pentanol and isodecanol. Particularly suitable alcohols are linear and branched primary alcohols (including mixtures) such as produced by the "Oxo" reaction of $C_3$ to $C_{20}$ olefins. The alcohols may also be cycloaliphatic such as cyclopentanol, cyclohexanol, cycloheptanol, cyclooctanol, as well as aromatic substituted aliphatic alcohols such as benzyl alcohol, phenylethyl alcohol, and phenylpropyl alcohol. Other aliphatic structures include 2-methoxyethanol and the like.

Phenols include alkylphenols of up to 30 carbons such as p-methylphenol, p-ethylphenol, p-butylphenol, p-heptylphenol, p-nonylphenol, dinonylphenol and P-decylphenol. The aromatic radicals may contain other substituents such as halide atoms.

Alcohols (polyols) having 2 or more hydroxyl groups, e.g., about two to six hydroxyl groups and have 2 to 30 carbons, include glycols such as ethylene glycol, propylene glycol, butylene glycol, pentylene glycol, hexylene glycol, neopentylene glycol, decylene glycol, diethylene glycol, triethylene glycol and dipropylene glycol. Other polyols include glycerine, 1,3-propanediol, pentaerythritol, galactitol, sorbitol, mannitol, erythritol, trimethylolethane and trimethylolpropane.

Carboxylic acids include formic acid, acetic acid, propionic acid, butyric acid, valeric acid, caproic acid, caprylic acid, capric acid, lauric acid, myristic acid, palmitic acid, stearic acid, oleic acid, linoleic acid and linolenic acid. Other carboxylic acids include benzoic acid, cyclohexane carboxylic acid, phenylacetic acid, toluic acid, chlorobenzoic acid, bromobenzoic acid, nitrobenzoic acid, phthalic acid, isophthalic acid, terephthalic acid, salicylic acid, hydroxybenzoic acid, anthranilic acid, aminobenzoic acid, methoxybenzoic acid and the like.

Amines include methylamine, dimethylamine, ethylamine, diethylamine, n-propylamine, di-n-propylamine, isopropylamine, n-butylamine, isobutylamine, cyclohexylamine, piperazine, benzylamine, phenylethylamine, monoethanolamine, diethanolamine, aminoethylethanolamine, ethylenediamine, diethylenetriamine, triethylenetetramine, tetraethylenepentamine, pentaethylenehexamine, tetramethylenediamine and hexamethylenediamine. Other amines include aniline, methylaniline, toluidine, anisidine, chloroaniline, bromoaniline, nitroaniline, diphenylamines, phenylenediamine, benzidine, aminobenzoic acid, sulfanilic acid and sulfanilamide. Still other amines include acetanilide, benzanilide, aceto-toluidide, nitroacetanilide and the like.

Preferred active hydrogen-containing compound starting materials which can be employed in the step (i) transesterification reaction include any permissible active hydrogen-containing organic compounds such as those embraced by the formula $R(OH)_q$ wherein R is the residue of an organic compound and q is a value which satisfies the valencies of R, preferably q is a value of from 1 to about 6, more preferably q is a value of from 1 to about 4. Preferred active hydrogen-containing compound starting materials include monohydric, dihydric and polyhydric alcohols. Illustrative active hydrogen-containing compound starting materials useful in this invention include, for example, ethylene glycol, diethylene glycol, triethylene glycol, tetraethylene glycol, pentaethylene glycol, hexaethylene glycol, polyethylene glycols, $C_1$-$C_{20}$ alcohols including mixtures thereof, 2-(2-butoxyethoxy)ethanol, 2-(2-methoxyethoxy)ethanol, 2-methoxyethanol, poly(oxyethylene)-glycols such as CARBOWAX ® poly(oxyethylene)-glycols, UCON ® fluid and lubricant materials, ethylenediamine, piperazine, N,N-dimethylethanolamine and the like.

Suitable alkylene carbonate starting materials which can be employed in the step (i) transesterification reaction include any permissible substituted or unsubstituted alkylene carbonate(s) which is capable of reacting with an active hydrogen-containing compound under the process conditions described herein, such as ethylene carbonate, propylene carbonate, trimethylene carbonate and the like including mixtures thereof. Other suitable alkylene carbonate starting materials include those derived from gem-1,2-diols. Preferred alkylene carbonates include, for example, ethylene carbonate, propylene carbonate, trimethylene carbonate and the like. The mole ratio of alkylene carbonate to active hydrogen-containing compound is not narrowly critical and can vary over a wide range, for example, from about 0.5:1 or less to about 1000:1 or greater.

The step (i) transesterification reaction can be conducted over a wide range of pressures ranging from atmospheric or subatmospheric pressures to superatmospheric pressures. However, the use of very high pressures has not been observed to confer any significant advantages but increases equipment costs. Further, it is preferable to conduct the step (i) reaction at reduced pressures of from about 1 mm Hg to less than about 760 mm Hg. The step (i) transesterification reaction is preferably effected in the liquid or vapor states or mixtures thereof.

The temperature of the step (i) transesterification reaction may be as low as about ambient temperature to about 200° C. Preferably, the reaction temperature ranges from about 50° C. to about 150° C., and most preferably from about 60° C. to about 120° C.

Suitable carboxylated alkoxylated active hydrogen-containing compounds prepared by the step (i) transesterification reaction include any permissible substituted or unsubstituted carboxyl-containing alkoxylated active hydrogen-containing compounds which are capable of eliminating carbon dioxide under the process conditions described herein, e.g., esters, carbonates, carbamates and the like, such as those embraced by the formula $R_1[(CHR_2-CHR_3OC(O)O)_dH]_b$ wherein $R_1$ is an organic residue of an organic compound having at least one active hydrogen, b is an integer of at least 1 up to the number of active hydrogens contained by the organic compound, $R_2$ and $R_3$ may be the same or different and can be hydrogen and alkyl (including hydroxy- and halo-substituted alkyl) of, for example, 1 to 28 carbons, and d is an integer of at least 1, say, 1 to about 50. Illustrative carboxylated alkoxylated active hydrogen-containing compounds include for example, surfactant (poly)carbonates such as TERGITOL ® nonionic surfactant (poly)carbonates, poly(oxyalkylene)glycol (poly)carbonates such as CARBOWAX ® poly(oxyethylene)glycol (poly)carbonates, poly(oxyethylene)(oxypropylene)glycol (poly)carbonates, alkoxy and allyloxy poly(oxyethylene)(oxypropylene)glycol (poly)-carbonates, alkoxy and allyloxy poly(oxyalkylene)-glycol (poly)carbonates, 2-methoxyethyl carbonate, 2-(2-methoxyethoxy)ethyl carbonate and the like. The amount of carboxylated alkoxylated active hydrogen-containing compound(s) employed in step (ii) is dependent on the amount of mixed metal oxide catalyst employed.

The carboxylated alkoxylated active hydrogen-containing compounds prepared by the step (i) transesterification reaction may undergo one or more transesterifications prior to the step (ii) decarboxylation reaction. For example, an active hydrogen-containing compound different from the active hydrogen-containing compound starting material may be reacted with the originally prepared carboxylated alkoxylated active hydrogen-containing compound under conditions effective to prepare a different carboxylated alkoxylated active hydrogen-containing compound. Suitable active hydrogen-containing compounds include those embraced by the formula $R_4OH$ wherein $R_4$ is the residue of an organic compound. This invention is not intended to be limited in any manner by the step (i) transesterification reaction.

Step (ii) of certain processes of this invention can in general be referred to as a decarboxylation reaction. Suitable decarboxylation catalysts which can be employed in step (ii) include two or more metal oxides. A magnesium:aluminum mixed metal oxide is a preferred mixed metal oxide catalyst as more fully described below. Both homogeneous and heterogeneous catalysts can be employed in the step (ii) reaction. The amount of decarboxylation catalyst used in step (ii) is not narrowly critical and is dependent on whether step (ii) is conducted batchwise or continuously. If batchwise, the catalyst employed can range from about 0.01 weight percent or less to about 10 weight percent or greater of the total weight of the starting materials. If continuously, generally a fixed bed is employed.

Suitable decarboxylation catalysts for use in the processes of this invention comprise mixed metal oxides containing two or more metal oxides. Illustrative of such metal oxides include, for example, two or more of the following: Group IA metal oxides, Group IIA metal oxides, Group IIIB metal oxides (including lanthanides and actinides), Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides. Certain of these metal oxide(s) may also be used as transesterification catalysts in accordance with this invention such as Group IIA and/or IIIA metal oxides. Preferred mixed metal oxides are amphoteric or basic. Preferred mixed metal oxides which may be utilized as decarboxylation catalysts include, for example, one or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

Group IIA metal oxides such as magnesium oxide and calcium oxide and Group IIIA metal oxides such as aluminum oxide and gallium oxide are preferred mixed metal oxides for use in this invention. For mixed metal oxides in which at least one of the metals is magnesium, suitable metals in association with magnesium may include, for example, one or more of the following: Group IIIA metals such as boron, aluminum, gallium and indium, Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IVA metals such as silicon, germanium, tin and lead, Group VA metals such as arsenic, antimony and bismuth, and Group IVB metals such as zirconium and hafnium. For mixed metal oxides in which at least one of the metals is calcium, suitable metals in association with calcium may include, for example, one or more of the following: Group IIIA metals such as boron, aluminum, gallium and indium, Group IVA metals such as silicon, germanium, tin and lead, Group VB metals such as niobium and tantalum, and Group VIB metals such as chromium, molybdenum and tungsten. Illustrative of mixed metal oxides which may be used as decarboxylation catalysts include, for example, $MgO-Al_2O_3$, $MgO-SiO_2$, $MgO-CdO$, $MgO-Bi_2O_3$, $MgO-Sb_2O_5$, $MgO-SnO_2$, $MgO-ZrO_2$, $MgO-BeO$, $MgO-TiO_2$, $MgO-CaO$, $MgO-SrO$, $MgO-ZnO$, $MgO-Ga_2O_3$, $MgO-Y_2O_3$, $MgO-La_2O_3$, $MgO-MoO_3$, $MgO-Mn_2O_3$, $MgO-Fe_2O_3$, $MgO-Co_3O_4$, $MgO-WO_3$, $MgO-V_2O_5$, $MgO-Cr_2O_3$, $MgO-ThO_2$, $MgO-Na_2O$, $MgO-BaO$, $MgO-CaO$, $MgO-HfO_2$, $MgO-Li_2O$, $MgO-Nb_2O_5$, $MgO-Ta_2O_5$, $MgO-Gd_2O_3$, $MgO-Lu_2O_3$, $MgO-Yb_2O_3$, $MgO-CeO_2$, $MgO-Sc_2O_3$, $MgO-PbO$, $MgO-NiO$, $MgO-CuO$, $MgO-CoO$, $MgO-B_2O_3$, $CaO-SiO_2$, $CaO-Al_2O_3$, $CaO-SnO$, $CaO-PbO$, $CaO-Nb_2O_5$, $CaO-Ta_2O_5$, $CaO-Cr_2O_3$, $CaO-MoO_3$, $CaO-WO_3$, $CaO-TiO_2$, $CaO-HfO_2$, $MgO-SiO_2-Al_2O_3$, $MgO-SiO_2-ZnO$, $MgO-SiO_2-ZrO_2$, $MgO-SiO_2-CuO$, $MgO-SiO_2-CaO$, $MgO-SiO_2-Fe_2O_3$, $MgO-SiO_2-B_2O_3$, $MgO-SiO_2-WO_3$, $MgO-SiO_2-Na_2O$, $MgO-SiO_2-Ga_2O_3$, $MgO-SiO_2-La_2O_3$, $MgO-SiO_2-Nb_2O_5$, $MgO-SiO_2-Mn_2O_3$, $MgO-SiO_2-Co_3O_4$, $MgO-SiO_2-NiO$, $MgO-SiO_2-PbO$, $MgO-SiO_2-Bi_2O_3$, $MgO-Al_2O_3-ZnO$, $MgO-Al_2O_3-ZrO_2$, $MgO-Al_2O_3-Fe_2O_3$, $MgO-Al_2O_3-WO_3$, $MgO-Al_2O_3-La_2O_3$, $MgO-Al_2O_3-Co_3O_4$, $CaO-SiO_2-Al_2O_3$, $CaO-SiO_2-SnO$, $CaO-SiO_2-Nb_2O_5$, $CaO-SiO_2-WO_3$, $CaO-SiO_2-TiO_2$, $CaO-SiO_2-MoO_3$, $CaO-SiO_2-HfO_2$, $CaO-SiO_2-Ta_2O_5$, $CaO-Al_2O_3-SiO_2$, $CaO-Al_2O_3-PbO$, $CaO-Al_2O_3-Nb_2O_5$, $CaO-Al_2O_3-WO_3$, $CaO-Al_2O_3-TiO_2$, $CaO-Al_2O_3-MoO_3$, $CaO-HfO_2-Al_2O_3$, $CaO-HfO_2-TiO_2$, and the like. Other suitable mixed metal oxides embraced within the scope of this invention are disclosed by Tanabe et al., Bulletin of the Chemical Society of Japan, Vol. 47(5), pp. 1064–1066 (1974).

The mixed metal oxides described herein which can be used as decarboxylation catalysts may contribute to product selectivity and/or catalytic activity of the reaction and/or stability of the catalyst. As discussed hereinafter, the decarboxylation catalyst employed in this invention may also contain support(s), binding agent(s) or other additives to stabilize or otherwise help in the manufacture of the catalyst.

The decarboxylation catalysts which comprise two or more metal oxides may be prepared in a wide variety of ways. For example, the two or more metal oxides can be provided from metal salts which can either be heated or precipitated to form the mixed metal oxides. Also, two or more metal oxides may be provided as a partial condensate on a support, such as a silica or alpha, beta or gamma alumina, silicon carbide, and the like, and then condensed by heating to effect polymerization to the desired oxide form. The two or more metal oxides may be condensed from hydrolyzable monomers to the desired oxides, indeed, to form oxide powders which can thereafter be compressed in the presence of a condensation catalyst to form pellets and larger structures of the mixed metal oxide decarboxylation catalyst. A blend of the powders and condensation catalyst can be made into a shapeable paste which can be extruded and cut into pellets according to conventional procedures. The extrudate may thereafter be fired to cure the condensation catalyst and fix the structure. The cut extrudate may be blended with a support material such as those characterized above, and the blend fired to fuse the mixed metal oxide catalyst to the support.

In an embodiment of this invention, a magnesium salt, e.g., magnesium nitrate, and an aluminum salt, e.g., aluminum nitrate, are precipitated using ammonium hydroxide. The material is then washed with deionized water and calcined at a temperature of from about 350° C. to about 450° C. to afford the desired magnesium:aluminum mixed metal oxide catalyst.

In another embodiment, a magnesium oxide, e.g., magnesium carbonate hydroxide pentahydrate, and an aluminum oxide, e.g., aluminum hydroxide hydrate, are added to deionized water and thoroughly mixed to form a paste. The paste is then calcined at a temperature of from about 350° C. to about 450° C. to afford the desired magnesium:aluminum mixed metal oxide catalyst.

A typical catalyst structure comprises a Group IIA and IIIA mixed metal oxide having a surface area of at least about 100 m²/gm which may or may not be bonded to a support material. The decarboxylation catalysts on a support preferably have a surface area greater than about 20 m²/gm to as high as about 260 m²/gm, or greater depending upon which metal oxides are employed. In the case of magnesium:aluminum oxides, the surface area can be greater than about 50 m²/gm to as high as about 260 m²/gm, more preferably, greater than about 100 m²/gm to as high as about 260 m²/gm, determined according to the single point $N_2$ method.

The term "support," as used herein and in the claims, means a solid structure which does not adversely affect the catalytic properties of the catalyst and is at least as stable as the catalyst to the reaction medium. The support can function as a decarboxylation catalyst independent of the mixed metal oxide catalyst used herein, although it may have lower catalytic activity to the reaction. The support may act in concert with the catalyst to moderate the reaction. Some supports may contribute to the selectivity of the reaction. The catalyst structure can comprise from about 2 to about 60 percent by weight or greater of the support, more preferably from about 10 to about 50 percent by weight of the support, the remainder being the weight of the mixed metal oxides. Included in the weight of the support is the weight of any binding agent such as phosphates, sulfates, silicates, fluorides, and the like, and any other additive provided to stabilize or otherwise help in the manufacture of the catalyst. The support may be particles as large or larger than the catalyst component and "glued" to the decarboxylation catalyst by virtue of a binding medium.

The support may constitute a separate phase in the process of extruding the catalytic structure. In this embodiment, the support forming material, preferably as a paste is blended with a paste of the decarboxylation catalyst or a partial condensate thereof. The paste may comprise the oxide forms of the support and the decarboxylation catalyst, each blended with water, and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the mixed metal oxide decarboxylation catalyst.

A preferred group of mixed metal oxide catalysts for use in this invention include materials having the formula:

$$M_x^{2+} Q_y^{3+} (OH)_{2x+3y-nz} A_z^{n-} \cdot a\, H_2O \qquad (I)$$

wherein M is at least one divalent metal cation; Q is at least one trivalent metal cation; and A is at least one anion providing a valence (n−), wherein n is at least 1, e.g., between 1 and 4 and most often between 1 and 3, and wherein a is a positive number, M, Q, and A are provided in a proportion such that x/y is a number equal to or greater than 1, z has a value greater than zero and 2x+3y−nz is a positive number. M, Q and A may be selected to Provide a layered structure. Preferably, x/y is in the range of 1 to 12, more preferably x/y is in the range of 1 to 6 and most preferably is in the range of 1 to 4. Preferably, z has a value such that x/z is between n and 12n, more preferably between n and 6n and most preferably between n and 4n.

Suitable divalent metal cations, M, broadly include elements selected from the Transition elements and Groups IIA and IVA of the Periodic Table as well as certain Group IIIB elements. As specific examples can be mentioned magnesium, calcium, titanium, vanadium, chromium, manganese, iron, cobalt, nickel, palladium, platinum, copper, zinc, cadmium, mercury, tin and lead. Divalent metal cations which are particularly suitable are magnesium, nickel, cobalt, zinc, calcium, strontium and copper. Suitable trivalent metal cations, Q, broadly include elements selected from the Transition elements and Groups IIIA and VA of the Periodic Table as well as certain Group IIIB elements. As specific examples can be mentioned aluminum, antimony, titanium, scandium, bismuth, vanadium, yttrium, chromium, iron, manganese, cobalt, ruthenium, nickel, gold, gallium, thallium, and cerium. Trivalent metal cations which are particularly suitable can be selected from aluminum, boron, gallium and lanthanum.

The composition of formula (I) also can include a wide range of anions, A. Any anion or combination of anions which can balance the charge of the cations can be used. Suitable anions include inter alia, halides (such as chloride, fluoride, bromide, and iodide), nitrite, nitrate, sulfite, sulfate, sulfonate, carbonate, chromate, cyanate, phosphite, phosphate, molybdocyanate, bicarbonate, hydroxide, arsenate, chlorate, ferrocyanide, borate, cyanide, cyanaurate, cyanaurite, ferricyanide, selenate, tellurate, bisulfate, as well as organic anions such as oxalate, acetate, hexanoate, sebacate, formate, benzoate, malonate, lactate, oleate, salicylate, stearate, citrate, tartrate, maleate, and the like. The class of metalate anions described in U.S. Pat. No. 4,667,045, including metavanadate, orthovanadate, molybdate, tungstate, hydrogen pyrovanadate and pyrovanadate, also are suitable as anion A. Anions suitable for use in combination with the metal cations previously identified as being particularly suitable are carbonate, halide, phosphate, chromate, sulfate, hydroxide, oxalate, acetate, nitrate, hexanoate, sebacate, vanadate, molybdate, tungstate and ferrocyanate.

The foregoing lists of suitable divalent and trivalent cations and suitable anions are meant to be illustrative and not exclusive. Those skilled in the art will recognize that other cations and anions can be used provided that the specific type of cations and their relative amounts (x/y ratio) and the specific type of anions and their relative amount result in a mixed metal oxide composition.

Included in the materials identified above are those based on exchangeable anionic clay minerals. For example, compositions of formula (I) wherein M is magnesium and Q is aluminum are related to hydrotalcites, while compositions in which M is nickel and A is aluminum are related to takovites. In fact, mixed metal oxides prepared using magnesium, nickel or cobalt as the divalent cation and aluminum as the trivalent cation exhibit the typical X-ray diffraction pattern of a hydrotalcite.

In another aspect, the processes of this invention can utilize mixed metal oxide catalyst compositions prepared by calcining at an elevated temperature compositions according to formula (I). Suitable calcined compositions have the general formula:

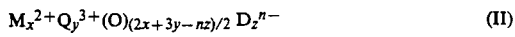

$$M_x{}^{2+}Q_y{}^{3+}(O)_{(2x+3y-nz)/2}D_z{}^{n-} \tag{II}$$

wherein M, Q, x, y, z and n have the same meanings defined above in connection with formula (I), and D is at least one nonvolatile anion. Nonvolatile anions may include, inter alia. halides, nitrates, phosphites, phosphate, vanadate, molybdate, tungstate, sulfite, sulfate, chromate, arsenate, borate, chlorate and the like. This list is illustrative and not exclusive.

Heat treating the formula (I) compositions to prepare the calcined mixed metal oxide compositions of formula (II) can be done, for example, at a temperature in the range of 200° C. to 800° C. for a period of time of about 12 to 24 hours under an inert atmosphere such as nitrogen or in appropriate cases under an oxidizing atmosphere such as air.

Calcination of the mixed metal oxide composition dehydrates the composition and converts at least partially the metal hydroxides to metal oxides. Any nonvolatile anions may be present in the calcined material.

Provided the calcination temperature is not excessive, the mixed metal oxide can be rehydrated to the mixed metal hydroxide with water. Generally, the mixed metal oxide can be restored readily if the calcination temperature does not exceed about 600° C. Mixed metal oxides which are calcined under more severe conditions are not easily rehydrated and lower surface area materials are obtained.

Certain compositions falling within formula (I), such as hydrotalcite, which comprises a magnesium-aluminum hydroxide carbonate, and takovite, which comprises a nickel-aluminum hydroxide carbonate, are naturally occurring compositions. However, such compounds, as well as their related compositions, also can be prepared synthetically from inexpensive starting materials using well-known coprecipitation techniques. Procedures for direct synthesis of such materials are described in Itaya et al., *Inorg. Chem* (1987) 6:624-626; Taylor, R. M., *Clay Minerals* (1984) 19:591-603; Reichle, U.S. Pat. No. 4,476,324; Bish, D. L., *Bull. Mineral* (1980), 103:170-175 and Miyata et al., *Clays and Clay Minerals* (1977), 25:14-18. Using direct synthesis one has the ability to vary within wide limits the $M^{+2}/Q^{+3}$ atomic ratio as well as the anion.

For example, a composition of formula (I) where $M^{+2}$ is nickel or magnesium, $Q^{+3}$ is aluminum and $A^{n-}$ is carbonate can be prepared by adding, as aqueous solutions, (a) a mixture of nitrates, sulfates or chlorides of nickel or magnesium and aluminum in a desired atomic ratio of nickel or magnesium to aluminum, e.g. 6 atoms of nickel as nickel chloride to 2 atoms of aluminum as aluminum chloride, to (b) an aqueous solution of a stoichiometric amount of sodium hydroxide and a water soluble salt of the desired anion, e.g., sodium carbonate. The two solutions are mixed at a temperature of about 25° C. to 35° C. with vigorous stirring over a several-hour period to produce a slurry. The slurry then is heated for about 18 hours at a temperature within the range of about 50° C. to 200° C. (preferably between about 60° C. to 75° C.) in order to control crystallization and the ultimate particle size of the resulting crystals. After filtering, and thorough washing and drying, the solids are recovered, typically as a powder.

As noted above, this procedure can be adapted to a wide variety of cations, cation atomic ratios and anion substitutions. For example, water soluble salts of divalent magnesium, cobalt, zinc, copper, iron and calcium can be substituted for the nickel chloride illustrated above, while water soluble salts of trivalent gallium and lanthanum can replace the aluminum chloride. A wide variety of other combinations also will be apparent to those skilled in the art. Generally, the rate of metal ion addition to the aqueous caustic/anion solution is not critical and can be varied widely. For example, a preferred preparation method is described in Schaper, H. et al., *Applied Catalyis*, 54, 1989, 79-90. the disclosure of which is incorporated herein by reference. The reaction temperature also is not critical, although the temperature during the reaction preferably is kept below about 100° C. An important feature of the procedure is the use of efficient agitation during the mixing procedure to avoid the formation of undesired by-products.

Loading of an anion A or D into the mixed metal oxide compositions is influenced by a variety of factors including (i) the amount of anion used in the preparation relative to the metal cations, (ii) the atomic ratio of the metal cations (x/y) in the preparation procedure, (iii) the size of the cations and anions and (iv) the preparation procedure. As used herein, "loading" is defined as the amount of available valences provided by a desired anion A or D expressed as a percentage of the total available valences for anion A or D. For example, carbonate loading in a hydrotalcite-type catalyst can be maximized by (i) using an excess (e.g., a greater than 3:1 molar ratio) of sodium carbonate to aluminum chloride during catalyst preparation and (2) adjusting the atomic ratio of magnesium to aluminum cations to about 2:1.

Mixed metal oxide compositions suitable as catalysts also can be prepared from the native or synthetic hydrotalcite-type compositions by ion exchange. For example, hydrotalcite can be treated at ambient conditions with 0.01N phosphoric acid for about 18 hours to replace the carbonate anion with phosphate anion. A halide analog of hydrotalcite prepared directly or by anion-exchange could be contacted with molybdic acid or a water soluble salt thereof, or with a water soluble salt of tungstic acid or vanadic acid in order to substitute the transition metal anion for the halide anion in the catalyst structure thereby to produce a mixed metal oxide composition of formula (I). Other ion exchanges will be apparent to those skilled in the art.

Calcined mixed metal oxide compositions may exhibit a higher level of selectivity/activity than uncalcined compositions. If a calcined mixed metal oxide catalyst composition experiences any decline in selectivity, it can be regenerated by a heat treatment in the presence of air to restore at least a portion of its initial level of selectivity/activity enhancement and reused. Conditions discussed above for calcining the hydrated mixed metal oxide compositions are suitable for regenerating compositions which have experienced a decline in activity.

Catalysts having the formulas (I) and (II) above wherein M is at least one of magnesium and calcium, Q is aluminum or gallium, A is at least one of carbonate, bicarbonate, phosphate, sulfate and nitrate, x/y is between 1 and 20, z has a value which satisfies the relationship: x/z is between n and 12n, and a is a positive number, are generally preferred for vapor phase decarboxylation due to their combination of activity (conversion of precursor) and selectivity. A preferred process involves a vapor phase process using mixed metal oxide catalyst wherein $M^{2+}$ is magnesium, $Q^{3+}$ is aluminum, $A^{n-}$ is carbonate, x/y is about 1, and z is about 1.

A group of mixed metal oxide catalyst compositions which can be employed in the processes of this invention is disclosed in copending U.S. Patent application Ser. No. 125,134, filed Nov. 25, 1987, the disclosure of which is incorporated herein by reference.

The step (ii) decarboxylation reaction may be effected in the liquid or vapor or supercritical liquid states or mixtures thereof. In this context, the vapor phase reaction is intended to refer to the general vapor state of the starting materials. Though the step (ii) decarboxylation reaction conditions may range from subatmospheric or atmospheric to superatmospheric conditions, it is desirable to run the step (ii) reaction from about 1 mm Hg to about 5,000 mm Hg, preferably from about 100 mm Hg to about 2,500 mm Hg.

The temperature of the step (ii) decarboxylation reaction may be as low as about 150° C. to about 500° C. Preferably, the reaction temperature ranges from about 175° C. to about 375° C., and most preferably from about 225° C. to about 350° C.

Suitable carboxylated alkoxylated active hydrogen-containing compounds for use in the step (ii) decarboxylation reaction can be prepared by the step (i) transesterification reaction or by other methods such as the carbonylation of active hydrogen-containing compounds with carbon monoxide and oxygen at elevated temperatures in the presence of certain copper salts. Such a carbonylation process can be an alternative to the step (i) transesterification reaction and is encompassed within the generic scope of this invention.

The step (ii) decarboxylation reaction can be conducted in the presence of an inert diluent which can be either a liquid or gas. When a liquid diluent is employed, it should preferably be a good solvent for the starting materials, inert under the reaction conditions, and of such a nature that separation from the alkoxylation product mixture will not be difficult. For instance, the boiling points of the diluent and the alkoxylation product mixture should differ by an adequate amount and there should be no tendency of the diluent to form an azeotrope with the desired alkoxylation product mixture.

Examples of useful liquid diluents that meet the foregoing qualifications include benzene, toluene, xylene, ethylbenzene, anisole, heptane, octane, nonane, decane, dibutyl ether, and the like. Hydrocarbons are preferred.

Illustrative gaseous diluents include for example, nitrogen, methane, hydrogen, carbon monoxide or carbon dioxide. The gaseous diluent should of course be chosen so that it does not prevent the preparation of the desired products.

While the use of such diluents may be beneficial, the processes of this invention can be operated using pure starting material(s) as a liquid or gaseous feed. The degree of dilution of the starting materials with various diluents may vary considerably depending upon any process constraints restricting the use of the diluent. For example, in commercial production, the use of very large quantities of some gaseous diluents may be disadvantageous due to the cost of pumping large volumes of the gaseous diluent and increased difficulty in isolating the product, which increase the energy costs of the process. With liquid diluents, the use of very large quantities may be disadvantageous due to the energy cost associated with large recovery and recycle. If the processes of this invention are to be carried out using a gaseous diluent, in general it is recommended that the starting material(s) constitute from about 1 to about 95, and preferably about 5 to about 50, mole percent of the starting material/carrier feed. Increasing the dilution of the starting material with a gaseous diluent such as hydrogen may tend to increase the selectivity of the reaction to the particular products desired. The amount of liquid diluent can vary widely, for instance, from no diluent to about 90 weight percent or greater of the total weight of the starting materials.

For processes of this invention in which an active hydrogen-containing compound and an alkylene carbonate are contacted in the presence of a mixed metal oxide catalyst under conditions effective to alkoxylate the active hydrogen-containing compound or other related processes described herein, it is understood that the process conditions described herein for the step (ii) decarboxylation reaction can desirably be employed for such processes.

The processes of this invention are useful for preparing substituted and unsubstituted alkoxylated active hydrogen-containing compounds such as those embraced by the formula $R_1[(CHR_2—CHR_3O)_dH]_b$ wherein $R_1$, $R_2$, $R_3$, d and b are as defined hereinabove. Illustrative alkoxylation product mixtures prepared by the processes of this invention include, for example, surfactants such as fatty alcohol ethoxylates and nonyl phenol ethoxylates, e.g., TERGITOL ® nonionic surfactants, poly(oxyalkylene)glycols such as CARBOWAX ® poly(oxyethylene)glycols and POLYOX ® poly(oxyethylene)glycols, CARBITOL ® materials, CELLOSOLVE ® materials, alkoxy and allyloxy poly(oxyalkylene)glycols, poly(oxyethylene)-(oxypropylene)glycols alkoxy and allyloxy poly(oxyethylene)(oxypropylene)glycols such as UCON ® fluids and lubricants, amine ethoxylates such as aminoethyethanolamine, 1-(2-hydroxyethyl)piperazine, 2-(dimethylaminoethoxy)ethanol and the like.

Illustrative of suitable alkoxylated active hydrogen-containing compounds which can be prepared by the processes of this invention include any permissible alkoxylated derivatives of described active hydrogen-containing compounds, which are described in Kirk-Othmer, Encyclopedia of Chemical Technology, Third Edition, 1984, the pertinent portions of which are incorporated herein be reference.

The alkoxylation product mixtures produced by the processes of this invention can be separated by distillation. For example, a crude reaction product can be subjected to a distillation-separation at atmospheric or reduced pressure through a packed distillation column. Reactive distillation may be useful in conducting the step (i) transesterification reaction.

The processes of this invention may be carried out using, for example, a fixed bed reactor, a fluid bed reactor, or a slurry reactor. The optimum size and shape of the catalyst will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the decarboxylation catalyst.

The processes are conducted for a period of time sufficient to produce the alkoxylation product mixtures. The exact reaction time employed is dependent, in part, upon factors such as temperature, nature and proportion of starting materials, and the like. The reaction time will normally be within the range of from about one-half to about 100 hours or more, and preferably from less than about one to about ten hours.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Illustrative of suitable reactants in effecting the processes of this invention include by way of example:

EC—ethylene carbonate
PC—propylene carbonate
TC—trimethylene carbonate
EG—ethylene glycol
AL—$C_8$-$C_{16}$ alcohol
DEG—diethylene glycol
PD—1,3-propanediol
GLY—glycerine
ME—methanol
EDA—ethylenediamine
DMA—dimethylamine
PIP—piperazine
DMEA—N,N-dimethylethanolamine
BA—n-butyl alcohol Illustrative of suitable products prepared by the processes of this invention include by way of example:

TER—TERGITOL ® nonionic surfactants
PEG—CARBOWAX ® poly(oxyethylene)glycols
POLX—POLYOX ® poly(oxyethylene)glycols
UC—UCON ® fluids and lubricants
MCE—2-methoxyethanol
MCA—2-(2-methoxyethoxy)ethanol
DMAEE—2-(dimethylaminoethoxy)ethanol
DMEA—N,N-dimethylethanolamine
POTD—poly(oxytrimethylene) derivatives
AEEA—aminoethylethanolamine
HEP—1-(2-hydroxyethyl)piperazine Illustrative of permissible reactions encompassed within the scope of this invention include, for example, the following reactant/product combinations:

| REACTANT(S) | PRODUCT(S) |
| --- | --- |
| AL, EC | TER |
| PD, TC | POTD |
| EG, EC | PEG |
| DEG, EC | PEG |
| EG, EC | POLX |
| DEG, EC | POLX |
| BA, EC, PC | UC |
| ME, EC | MCA |
| ME, EC | MCE |
| GLY, EC | PEG |
| PIP, EC | HEP |
| DMEA, EC | DMAEE |
| DMA, EC | DMEA |
| DMA, EC | DMAEE |
| EDA, EC | AEEA |

By this invention, alkoxylation product mixtures can be provided which have a narrow, but balanced distribution of alkoxylation species. These product mixtures can be relatively free from large amounts of substantially higher alkoxylation moieties, i.e, those having at least three more alkoxyl groups than the average peak alkoxylate specie. Advantageously, these narrow distributions can be obtained where the most prevalent alkoxylation moiety has four or greater alkoxy units, that is, in the regions in which conventional catalysts provide a relatively wide range of alkoxylation species.

The alkoxylation product mixtures prepared by the processes of this invention can be characterized as the reaction products of alkylene carbonates and organic compounds having at least one active hydrogen. The product mixtures can have at least one alkoxylation moiety which constitutes at least about 18, say, about 20 to 30 or 40, and most often about 20 to 30, weight percent of the composition. The alkoxylation mixtures of this invention also can have a relatively symmetrical distribution. Hence, the portion of the product mixture having three or more oxyalkylene unit groups (per active hydrogen site of the organic compound) than the peak alkoxylation specie can be relatively minor, e.g., often less than about 12, say, less than 10, and often about 1 to 10, weight percent of the mixture. Similarly, the alkoxylation species having fewer oxyalkylene groups (per active hydrogen site of the organic compound) by three or more oxyalkylene groups from the average peak alkoxylation specie can usually be relatively minor, e.g., less than about 15, say, less than about 10, often about 0.5 to 10, weight percent of the composition. Generally, the one oxyalkylene unit higher and the one oxyalkylene unit lower alkoxylates in respect to the most prevalent alkoxylation specie can be present in a weight ratio to the most prevalent alkoxylation specie of about 0.6:1 to 1:1.

Preferred alkoxylation product mixtures of this invention can correspond to the formula $$P_m = A' \times e^{-(m-\bar{m})^2/(2.6 + 0.4\bar{m})}$$

wherein m is the number of oxyalkylene groups per reactive hydrogen site for an alkoxylation specie (m must equal at least one) of the composition, $\bar{m}$ is the weight average oxyalkylene number, $A'$ is the weight percent of the most prevalent alkoxylation specie in the mixture and $P_m$ is, within plus or minus two percentage points, the weight percent of the alkoxylation specie having m oxyalkylene groups (per active hydrogen site) in the mixture. This distribution relationship generally applies where m is between the amount of $\overline{m}$ minus 4 to the amount of $\overline{m}$ plus 4.

For purposes herein, the average peak alkoxylation specie is defined as the number of oxyalkylene groups (per active hydrogen site) of the most prevalent alkoxylation specie when the next higher and lower homologs are each present in a weight ratio to the most prevalent alkoxylation specie of less than 0.9:1. When one of the adjacent homologs is present in a weight ratio greater than that amount, the average peak alkoxylation specie has an amount of oxyalkylene groups equal to the number average of those of the two species. The weight average oxyalkylene number is the weight average of the oxyalkylene groups of the alkoxylation species in the mixture (including unreacted alcohol), i.e., $\overline{m}$ equals the sum of $(m)(P_m)$ for all the species present divided by 100.

While the processes described herein can be capable of selectively providing narrow distributions of alkoxylates with the most prevalent having as low as one mole of oxyalkylene per mole of active hydrogen site, a particular advantage can exist in the ability to provide a narrow distribution at higher levels of alkoxylation, e.g., wherein the most prevalent specie has at least 4 oxyalkylene units. For some surfactant applications, the most prevalent alkoxylation specie can have 6, 7, 8, 9, 10, 11 or 12 oxyalkylene units per active hydrogen site. For many surfactant applications, it has been found that a relatively few species provide the desired activity, i.e., a range of plus or minus two oxyalkylene units. Hence, the compositions of this invention are particularly attractive in that the range of alkoxylation can be narrow, but not so narrow that a range of activity is lost.

Moreover, the relatively symmetrical distribution of alkoxylate species that can be provided by this invention enhances that balance while providing a mixture that can exhibit desirable physical properties such as cloud point, freeze point, viscosity, pour point and the like. For many alkoxylation mixtures of this invention, the species falling within the range of $\overline{m}$ plus or minus two can comprise at least about 75, say, about 80 to 95, sometimes 85 to 95, weight percent of the composition. Importantly, the compositions can be provided such that no single alkoxylation product is in an amount of greater than 50 weight percent of the composition, and, most often, the most prevalent specie can be in an amount of 20 to about 30 weight percent, e.g., about 22 to 28, weight percent, to enhance the balance of the composition.

Among the most commercially important alkoxylation products are those which utilize water or an alcohol (monols, glycols, polyols, etc.) as starter (initiator) and ethylene carbonate, propylene carbonate, or an ethylene carbonate/propylene carbonate mixture as the alkylene carbonate. Such alcohol ethoxylates encompass a myriad of structures, compositions and molecular weights intended for service in a diversity of applications ranging from heavy duty industrial end uses such as solvents and functional fluids to ultra-sophisticated, consumer-oriented end uses such as in pharmaceutical, personal care and household goods. The mixed metal oxide catalysts utilized herein find utility in the manufacture of a broad range of alkoxylation products, but are particularly useful in the manufacture of alkoxylates designed for service in sophisticated, consumer-oriented end use areas of application where product quality demands are stringent. Among the many types of alkoxylates which are used in such applications, two of the most prominent are the poly(oxyethylene)glycols and the fatty alcohol ethoxylates. The poly(oxyethylene)- glycols, known under such tradenames as CARBOWAX®, POLYGLYCOL E®, PLURACOL E®, etc., are manufactured by ethoxylation of ethylene glycol or one of its homologues; they are produced over a molecular weight range of about weight range of about 200 to about 8,000. The fatty alcohol ethoxylates, known under such nonionic surfactant tradenames as NEODOL®, ALFONIC®, TERGITOL®, etc., are manufactured by ethoxylation of linear or branched $C_{10}$-$C_{16}$ saturated alcohols; they are produced over a molecular weight range of about 300 to about 800.

As used herein, the phrase "residue of an organic compound" is contemplated to include all permissible residues of organic compounds. In a broad aspect, the permissible residues include acyclic and cyclic, branched and unbranched, carbocyclic and heterocyclic, aromatic and nonaromatic residues of organic compounds. Illustrative organic compound residues include, for example, alkyl, aryl, cycloalkyl, heterocycloalkyl, alkyl(oxyalkylene), aryl(oxyalkylene), cycloalkyl(oxyalkylene), heterocycloalkyl-(oxyalkylene), hydroxy(alkyleneoxy) and the like. The permissible residues can be substituted or unsubstituted and the same or different for appropriate organic compounds. This invention is not intended to be limited in any manner by the permissible residues of organic compounds.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

What is claimed is:

1. A process for the alkoxylation of an active hydrogen-containing compound comprising contacting the active hydrogen-containing compound with an alkylene carbonate in the presence of a mixed metal oxide catalyst under conditions effective to alkoxylate the active hydrogen-containing compound; wherein the product is characterized by a mixture having at least one alkoxylation moiety which constitutes about 18 to 40 weight percent of the mixture; the weight percent of the mixture having three or more oxyalkylene units than the average peak alkoxylation specie is less than about 12 weight percent of the mixture; the alkoxylation specie having one oxyalkylene group more than that of the most prevalent specie and the alkoxylation specie having one oxyalkylene group less than that of the most prevalent specie are present in a weight ratio to the most prevalent specie of about 0.6:1 to 1:1.

2. The process of claim 1 wherein the active hydrogen-containing compound comprises a substituted or unsubstituted alcohol, phenol, carboxylic acid, amine, thiophenol, mercaptan or amide.

3. The process of claim 1 wherein the active hydrogen-containing compound comprises an alcohol.

4. The process of claim 3 wherein the alcohol comprises a monohydric, aliphatic alcohol having from 1 to 7 carbons.

5. The process of claim 4 wherein the monohydric, aliphatic alcohol is selected from methanol, 2-methoxyethanol and 2-(2-methoxyethoxy)ethanol.

6. The process of claim 3 wherein the alcohol comprises a dihydric alcohol.

7. The process of claim 6 wherein the dihydric alcohol is ethylene glycol.

8. The process of claim 3 wherein the alcohol comprises a polyhydric alcohol.

9. The process of claim 8 wherein the polyhydric alcohol is glycerine.

10. The process of claim 3 wherein the alcohol comprises a monohydric, aliphatic alcohol having from 8 to 20 carbons.

11. The process of claim 10 wherein the monohydric, aliphatic alcohol is selected from n-dodecanol, a mixture of $C_8$–$C_{10}$ alcohols and a mixture of $C_{12}$–$C_{14}$ alcohols.

12. The process of claim 3 wherein the alcohol is a product of a hydroformylation/hydrogenation reaction.

13. The process of claim 1 wherein the active hydrogen-containing compound comprises an amine.

14. The process of claim 13 wherein the amine comprises ethylenediamine, piperazine or N,N-dimethylethanolamine.

15. The process of claim 1 wherein the alkylene carbonate comprises a substituted or unsubstituted alkylene carbonate.

16. The process of claim 1 wherein the alkylene carbonate comprises ethylene carbonate, propylene carbonate, trimethylene carbonate or mixtures thereof.

17. The process of claim 1 wherein the mixed metal oxide catalyst comprises two or more Group IA metal oxides, Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides.

18. The process of claim 17 wherein the mixed metal oxide catalyst comprises two or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

19. The process of claim 1 wherein the mixed metal oxide catalyst comprises at least one Group IIA metal oxide.

20. The process of claim 1 wherein the mixed metal oxide catalyst comprises a Group IIA metal oxide and a Group IIIA metal oxide.

21. The process of claim 1 wherein the mixed metal oxide catalyst comprises a Group IIA metal oxide and a Group IIIB metal oxide.

22. The process of claim 1 wherein the mixed metal oxide catalyst comprises magnesium oxide and aluminum oxide.

23. The process of claim 1 wherein the mixed metal oxide catalyst comprises a high surface area mixed metal oxide.

24. The process of claim 1 wherein the mixed metal oxide catalyst has a surface area greater than about 50 $m^2/gm$.

25. The process of claim 19 wherein the Group IIA metal oxide comprises from about 10 weight percent to about 90 weight percent of the weight of the catalyst.

26. The process of claim 1 wherein the mixed metal oxide catalyst is associated with a support material.

27. The process of claim 26 wherein the support comprises an alumina material or an alumina-silica material.

28. The process of claim 26 wherein the support comprises an silica material or a silica-alumina material.

29. The process of claim 26 wherein the support comprises from about 2 to about 50 percent by weight of the mixed metal oxide catalyst.

30. The process of claim 1 wherein the mixed metal oxide catalyst comprises:

(a) a material having the formula:

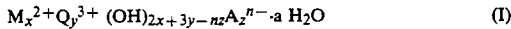

$$M_x^{2+}Q_y^{3+} (OH)_{2x+3y-nz}A_z^{n-} \cdot a\, H_2O \qquad (I)$$

wherein M is at least one divalent metal cation; Q is at least one trivalent metal cation; and A is at least one anion providing a valence (n−), wherein n is 1 to 4 and wherein a is a positive number, M, Q and A are provided in a proportion such that x/y is a number equal to or greater than 1, z has a value greater than zero and 2x+3y−nz is a positive number, or (b) a material prepared by calcining the material of formula (I) having the formula

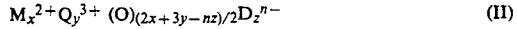

$$M_x^{2+}Q_y^{3+} (O)_{(2x+3y-nz)/2}D_z^{n-} \qquad (II)$$

wherein M, Q, x, y, z and n have the same meanings defined above in connection with formula (I), and D is at least one nonvolatile anion.

31. The process of claim 30 wherein x/y is a number between 1 and 12 and z has a value which satisfies the relationship: x/z is between n and 12n.

32. The process of claim 30 wherein A is selected from the group consisting of carbonate, halide, phosphite, phosphate, chromate, sulfate, hydroxide, oxalate, acetate, nitrate, hexanoate, sebacate, vanadate, molybdate, tungstate and ferrocyanate.

33. The process of claim 30 wherein D is selected from the group consisting of halides, phosphite, phosphate, vanadate, molybdate, tungstate, sulfite, sulfate, chromate, arsenate, borate and chlorate.

34. The process of claim 30 wherein x/y is a number between 1 and 6 and z has a value which satisfies the relationship: x/z is between n and 6n.

35. The process of claim 30 wherein said material prepared by calcining the material of formula (I) has been heat treated at a temperature in the range of 200° C. to 800° C. for 12 to 24 hours.

36. The process of claim 30 wherein M is magnesium and Q is aluminum.

37. The process of claim 1 wherein the product comprises 2-methoxyethanol, 2-(2-methoxyethoxy)ethanol, a fatty alcohol ethoxylate, a nonyl phenol ethoxylate, an alkoxy or allyloxy poly(oxyalkylene)glycol, an alkoxy or allyloxy poly(oxyethylene)(oxypropylene)glycol, a poly(oxyalkylene)glycol, a poly(oxyethylene)-(oxypropylene)glycol or an amine ethoxylate.

38. The process of claim 37 wherein the amine ethoxylate comprises aminoethylethanolamine, 1-(2-hydroxyethyl)pip-erazine or 2-(dimethylaminoethoxy)ethanol.

39. The process of claim 1 wherein the ratio of moles of alkylene carbonate to moles of active hydrogen-containing compound is from about 0.5:1 to about 1000:1 or greater.

40. The process of claim 1 wherein the product comprises a mixture which has an alkoxylation specie distribution corresponding to the formula $$P_m = A' \times e^{-(m-\overline{m})2/(2.6+0.4\overline{m})}$$

wherein m is an integer of at least one and is the number of oxyalkylene groups per reactive hydrogen site of the alcohol for the alkoxylation specie, $\overline{m}$ is the weight average oxyalkylene number of the mixture, A' is the weight percent of the most prevalent alkoxylation specie in the mixture and Pm is, within plus or minus two percentage points, the weight percent of the alkoxylation specie having m oxyalkylene groups per active hydrogen site, based on the weight of the mixture.

41. A process for preparing an alkoxylated active hydrogen-containing compound which comprises (i) contacting an active hydrogen-containing compound with an alkylene carbonate under conditions effective to produce a carboxylated alkoxylated active hydrogen-containing compound, and (ii) contacting the carboxylated alkoxylated active hydrogen-containing compound with a mixed metal oxide catalyst under conditions effective to decarboxylate the carboxylated alkoxylated active hydrogen-containing compound; wherein the product is characterized by a mixture having at least one alkoxylation moiety which constitutes about 18 to 40 weight percent of the mixture; the weight percent of the mixture having three or more oxyalkylene units than the average peak alkoxylation specie is less than about 12 weight percent of the mixture; the alkoxylation specie having one oxyalkylene group more than that of the most prevalent specie and the alkoxylation specie having one oxyalkylene group less than that of the most prevalent specie are present in a weight ratio to the most prevalent specie of about 0.6:1 to 1:1.

42. The process of claim 41 wherein the active hydrogen-containing compound comprises a substituted or unsubstituted alcohol, phenol, carboxylic acid, amine, thiophenol, mercaptan or amide.

43. The process of claim 41 wherein the active hydrogen-containing compound comprises an alcohol.

44. The process of claim 41 wherein the alcohol comprises a monohydric, aliphatic alcohol having from 1 to 7 carbons.

45. The process of claim 44 wherein the monohydric, aliphatic alcohol is selected from methanol, 2-methoxyethanol and 2-(2-methoxyethoxy)ethanol.

46. The process of claim 43 wherein the alcohol comprises a dihydric alcohol.

47. The process of claim 46 wherein the dihydric alcohol is ethylene glycol.

48. The process of claim 43 wherein the alcohol comprises a polyhydric alcohol.

49. The process of claim 48 wherein the polyhydric alcohol is glycerine.

50. The process of claim 43 wherein the alcohol comprises a monohydric, aliphatic alcohol having from 8 to 20 carbons.

51. The process of claim 50 wherein the monohydric, aliphatic alcohol is selected from n-dodecanol, a mixture of $C_8$-$C_{10}$ alcohols and a mixture of $C_{12}$-$C_{14}$ alcohols.

52. The process of claim 43 wherein the alcohol is a product of a hydroformylation/hydrogenation reaction.

53. The process of claim 41 wherein the active hydrogen-containing compound comprises an amine.

54. The process of claim 53 wherein the amine comprises ethylenediamine, piperazine or N,N-dimethylethanolamine.

55. The process of claim 41 wherein the alkylene carbonate comprises a substituted or unsubstituted alkylene carbonate.

56. The process of claim 41 wherein the alkylene carbonate comprises ethylene carbonate, propylene carbonate, trimethylene carbonate or mixtures thereof.

57. The process of claim 41 wherein the carboxylated alkoxylated active hydrogen-containing compound comprises a substituted or unsubstituted carboxyl-containing alkoxylated active hydrogen-containing compound.

58. The process of claim 41 wherein the mixed metal oxide catalyst comprises two or more Group IA metal oxides, Group IIA metal oxides, Group IIIB metal oxides, Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides.

59. The process of claim 58 wherein the mixed metal oxide catalyst comprises two or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

60. The process of claim 41 wherein the mixed metal oxide catalyst comprises at least one Group IIA metal oxide.

61. The process of claim 41 wherein the mixed metal oxide catalyst comprises a Group IIA metal oxide and a Group IIIA metal oxide.

62. The process of claim 41 wherein the mixed metal oxide catalyst comprises a Group IIA metal oxide and a Group IIIB metal oxide.

63. The process of claim 41 wherein the mixed metal oxide catalyst comprises magnesium oxide and aluminum, oxide.

64. The process of claim 41 wherein the mixed metal oxide catalyst comprises a high surface area mixed metal oxide.

65. The process of claim 41 wherein the mixed metal oxide catalyst has a surface area greater than about 50 $m^2$/gm.

66. The process of claim 60 wherein the Group IIA metal oxide comprises from about 10 weight percent to about 90 weight percent of the weight of the catalyst.

67. The process of claim 41 wherein the mixed metal oxide catalyst is associated with a support material.

68. The process of claim 67 wherein the support comprises an alumina material or an alumina-silica material.

69. The process of claim 67 wherein the support comprises an silica material or a silica-alumina material.

70. The process of claim 67 wherein the support comprises from about 2 to about 50 percent by weight of the mixed metal oxide catalyst.

71. The process of claim 41 wherein the mixed metal oxide catalyst comprises:

(a) a material having the formula:

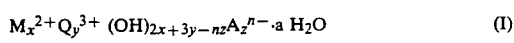
$$M_x^{2+}Q_y^{3+}(OH)_{2x+3y-nz}A_z^{n-}\cdot a\, H_2O \quad (I)$$

wherein M is at least one divalent metal cation; Q is at least one trivalent metal cation; and A is at least one anion providing a valence ($n^-$), wherein n is 1 to 4 and wherein a is a positive number, M, Q and A are provided in a proportion such that x/y is a number equal to or greater than 1, z has a value greater than zero and $2x+3y-nz$ is a positive number, (b) a material prepared by calcining the material of formula (I) having the formula $$M_x^{2+}Q_y^{3+}(O)_{(2x+3y-nz)/2}D_z^{n-} \quad (II)$$

wherein M, Q, x, y, z and n have the same meanings defined above in connection with formula (I), and D is at least one nonvolatile anion.

72. The process of claim 71 wherein x/y is a number between 1 and 12 and z has a value which satisfies the relationship: x/z is between n and 12n.

73. The process of claim 71 wherein A is selected from the group consisting of carbonate, halide, phosphite, phosphate, chromate, sulfate, hydroxide, oxalate, acetate, nitrate, hexanoate, sebacate, vanadate, molybdate, tungstate and ferrocyanate.

74. The process of claim 71 wherein D is from the group consisting of halides, phosphite, phosphate, vanadate, molybdate, tungstate, sulfite, sulfate, chromate, arsenate, borate and chlorate.

75. The process of claim 71 wherein x/y is between 1 and 6 and z has a value which satisfies the relationship: x/z is between n and 6n.

76. The process of claim 71 wherein said material prepared by calcining the material of formula (I) has been heat treated at a temperature in the range of 200° C. to 800° C. for 12 to 24 hours.

77. The process of claim 71 wherein M is magnesium and Q is aluminum.

78. The process of claim 41 wherein the product comprises 2-methoxyethanol, 2-(2-methoxyethoxy)ethanol, a fatty alcohol ethoxylate, a nonyl phenol ethoxylate, an alkoxy or allyloxy poly(oxyalkylene)glycol, an alkoxy or allyloxy poly(oxyethylene)(oxypropylene)glycol, a poly(oxyalkylene)glycol, a poly(oxyethylene)-(oxypropylene)glycol or an amine ethoxylate.

79. The process of claim 78 wherein the amine ethoxylate comprises aminoethylethanolamine, 1-(2-hydroxyethyl)piperazine or 2-(dimethylaminoethoxy)ethanol.

80. The process of claim 41 wherein the ratio of moles of alkylene carbonate to moles of active hydrogen-containing compound is from about 0.5:1 to about 1000:1 or greater.

81. The process of claim 41 wherein the product comprises a mixture which has an alkoxylation specie distribution corresponding to the formula

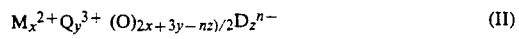
$$P_m = A' \times e^{-(m-\bar{m})^2/(2.6+0.4\bar{m})}$$

wherein m is an integer of at least one and is the number of oxyalkylene groups per reactive hydrogen site of the alcohol for he alkoxylation specie, $\bar{m}$ is the weight average oxyalkylene number of the mixture, $A'$ is the weight percent of the most prevalent alkoxylation specie in the mixture and $P_m$ is, within plus or minus two percentage points, the weight percent of the alkoxylation specie having m oxyalkylene groups per active hydrogen site, based on the weight of the mixture.

* * * * *